United States Patent [19]

Katoh et al.

[11] Patent Number: 4,783,466

[45] Date of Patent: Nov. 8, 1988

[54] NOVEL PYRIDINYLPYRIMIDINE DERIVATIVES, METHOD FOR PRODUCTION THEREOF AND A PLANT DISEASE PROTECTANT CONTAINING THEM AS THE ACTIVE INGREDIENT

[75] Inventors: Tsuguhiro Katoh, Osaka; Kiyoto Maeda; Masao Shiroshita, both of Hyogo; Norihisa Yamashita, Osaka; Yuzuru Sanemitsu; Satoru Inoue, both of Hyogo, all of Japan

[73] Assignee: Sumitomo Chemical Company, Limited, Osaka, Japan

[21] Appl. No.: 93,835

[22] Filed: Sep. 8, 1987

[30] Foreign Application Priority Data

Sep. 5, 1986 [JP] Japan .................................. 61-210010
Dec. 3, 1986 [JP] Japan .................................. 61-288349
Feb. 6, 1987 [JP] Japan .................................. 62-26762

[51] Int. Cl.$^4$ .................. A61K 31/505; C07D 239/20; C07D 239/72
[52] U.S. Cl. .................................. 514/256; 514/259; 544/253; 544/319; 544/333
[58] Field of Search ................ 544/284, 333; 514/256, 514/259, 319, 253

[56] References Cited

U.S. PATENT DOCUMENTS

| 3,992,380 | 11/1976 | Lesher et al. | 544/379 |
| 4,008,235 | 2/1977 | Lesher et al. | 544/328 |
| 4,018,770 | 4/1977 | Lesher et al. | 544/328 |
| 4,032,523 | 6/1977 | Lesher et al. | 544/328 |
| 4,166,117 | 8/1979 | Vincent et al. | 544/284 |
| 4,668,425 | 5/1987 | Nigorikawa et al. | 544/333 |

FOREIGN PATENT DOCUMENTS

| 2609208 | 9/1976 | Fed. Rep. of Germany | 544/320 |
| 53-46986 | 4/1978 | Japan | 544/320 |

OTHER PUBLICATIONS

W. Fife, "Cyabation in the Pyridine Series: ... Related Reactions", Heterocycles, vol. 22, No. 10 (1984), pp. 2375-2394.
W. Fife, "Regioselective Cyanation of Pyridine ... Reaction", J. Org. Chem., vol. 48, No. 8 (1983), pp. 1375-1377.
Vorbruggen et al, "Trimethylsilanol as Leaving Group; ... N-Heterocycles", Synthesis (1983), pp. 316-318.
E. Poziomek, "Experiments in the Synthesis of Pyridinium Amidines and Imino Esters," Journal Org. Chem., vol. 28 (1963), pp. 590-591.
Haginiwa, "Reactions Concernined ... Pyridine N-Oxide," Yakugaku Zasshi 95, (1) (1975), pp. 8-12 (Ref. CA 84(25) 18145S).
Kato et al, "Studies on Ketene and Its Derivatives ... 1,3-Oxazin-4-one Derivatives," Chem. Pharm. Bull., vol. 24 (2), (1976), pp. 356-359.
Lafferty et al, "The Preparation and Properties of Certain Pyridylpyrimidines ... Iron (II)," Journal Org. Chem., vol. 32, (1967) pp. 1591-1595.
Brown et al, "Unfused Heterobicycles as ... Thiazolylpyridines", Aust. J. Chem., vol. 33, (1980), pp. 2291-2298.
Brown et al, "Unfused Heterobicycles as Amplifiers ... Side Chains", Aust. J. Chem. vol. 35, (1982), pp. 1203-1207.
Singh et al, "Novel Rearrangement of ... Sodium Hydride", Heterocycles, vol. 22, No. 5, (1984), pp. 1133-1135.
Lesher et al, "Novel Orally Active Inhibitors of ... Malonates", J. Med. Chem., vol. 25, (1982), pp. 837-842.
Singh, "A Convenient and Efficient Conversion ... Transesterification", J. Hetero. Chem., vol. 21, (1984), pp. 247-248.
Singh et al, "Three Convenient and Novel Syntheses of 4-Amino-2-Arylpyrimidines", J. Hetero. Chem., vol. 14, (1977), pp. 1413-1414.

Primary Examiner—Mary C. Lee
Assistant Examiner—Zinna Northington
Attorney, Agent, or Firm—Sughrue, Mion, Zinn, Macpeak, and Seas

[57] ABSTRACT

A novel pyridinylpyrimidine derivative of the formula below, a method for preparation thereof and a plant disease protectant containing it,

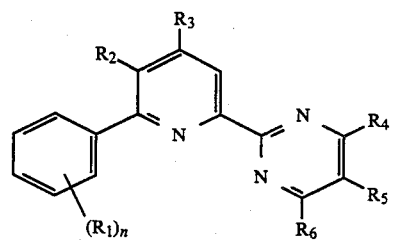

which is effective as a plant disease protectant.

17 Claims, No Drawings

NOVEL PYRIDINYLPYRIMIDINE DERIVATIVES, METHOD FOR PRODUCTION THEREOF AND A PLANT DISEASE PROTECTANT CONTAINING THEM AS THE ACTIVE INGREDIENT

This invention relates to a novel pyridinylpyrimidine derivative, a method for preparation thereof and a plant disease protectant containing it as an active ingredient.

The pyridinylpyrimidine derivatives such as 4-methyl-2-(2-pyridinyl)pyrimidine (J. Org. Chem. 32, 1591, (1967)) and N,N-dimethyl-2-(6-methyl-2-pyridylpyrimidine-4-yl-thio)-ethyl amine (Aust. J. Chem., 35 1203 (1982)) are known.

However, it is not known that the pyridinylpyrimidine derivatives have fungicidal effect at all.

An object of the present invention is to provide a compound having preventive and curative controlling effects against many plant diseases.

The present inventors have found that pyridinylpyrimidine derivatives having the formula (I) mentioned below or a salt thereof (hereinafter referred simply to as the present compound) have excellent fungicidal activity:

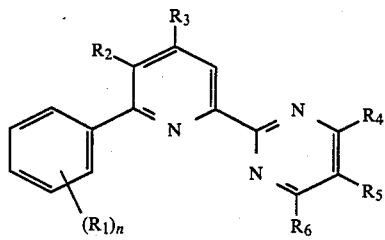
(I)

wherein $R_1$ may be the same or different and is lower alkyl such as $C_1$-$C_4$ alkyl, lower alkoxy such as $C_1$-$C_4$ alkoxy, lower haloalkyl whose alkyl is such as $C_1$-$C_4$ alkyl, or halogen (fluorine, chlorine, bromine or iodine); n is 0, 1, 2, 3, 4 or 5; $R_2$ and $R_3$, which may be the same or different, each represent hydrogen or lower alkyl such as $C_1$-$C_4$ alkyl; $R_4$ is hydrogen or lower alkyl such as $C_1$-$C_3$ alkyl; $R_5$ is hydrogen, lower alkyl such as $C_1$-$C_3$ alkyl or halogen (fluorine, chlorine, bromine or iodine), or $R_4$ and $R_5$ together represent a polymethylene group of the formula: $-(CH_2)_m-$ in which m is 3 or 4; and $R_6$ is hydrogen, lower alkyl such as $C_1$-$C_3$ alkyl, lower alkoxy such as $C_1$-$C_3$ alkoxy or lower alkylthio whose alkyl is such as $C_1$-$C_3$ alkyl.

Preferably, $R_1$ may be the same or different and is lower alkyl such as $C_1$-$C_3$ alkyl, lower alkoxy such as $C_1$-$C_3$ alkoxy, lower haloalkyl whose alkyl is such as $C_1$-$C_3$ alkyl, or halogen (fluorine, chlorine, bromine or iodine); n is 0, 1, 2 or 3; $R_2$ is hydrogen or methyl; $R_3$ is hydrogen or lower alkyl such as $C_1$-$C_4$ alkyl; $R_4$ is hydrogen, methyl or ethyl; $R_5$ is hydrogen, methyl, ethyl or halogen (fluorine, chlorine, bromine or iodine); and $R_6$ is hydrogen, methyl, ethyl, methoxy, ethoxy or methylthio.

More preferably, $R_1$ may be the same or different and is selected from methyl, ethyl, methoxy, $C_1$ or $C_2$ haloalkyl or halogen (fluorine or chlorine); n is 0, 1, 2 or 3; $R_2$ and $R_3$, which may be the same or different, each represent hydrogen or methyl; $R_4$ is methyl; $R_5$ is hydrogen or methyl; and $R_6$ is hydrogen, methyl or methoxy.

Most preferably, $R_1$ may be the same or different and is methyl, trifluoromethyl, fluorine or chlorine, n is 0, 1 or 2; $R_2$ is hydrogen or methyl; $R_3$ is hydrogen; $R_4$ is methyl; $R_5$ is hydrogen or methyl; and $R_6$ is hydrogen or methyl.

Plant disease that are controlled by the present compound include the followings;

Rice: *Pyricularia oryzae, Cochliobolus miyabeanus* and *Rhizoctonia solani;*

Barley and wheat: *Erysiphe graminis* f. sp. *hordei, E. graminis* f. sp. *tritici, Pyrenophora graminea, Puccinia striiformis, P. graminis, P. recondita, P. hordei, Pseudocercosphorella herpotrichoides, Rhynchosporium secalis, Septoria tritici* and *Leptosphaeria nodorum;*

Citrus: *Diaporthe citri* and *Elsinoe fawcetti;*

Apple: *Podosphaera leucotricha, Alternaria mali* and *Venturia inaequalis;*

Pear: *Venturia mashicola* and *Alternaria kikuchina;*

Peach: *Sclerotinia cinerea;*

Grape: *Elsinoe ampelina, Glomerella cingulata* and *Uncinula necator;*

Melon crops: *Colletotrichum lagenarium* and *Sphaerotheca fuliginea;*

Tomato: *Alternaria solani* and *Phytophthora infestans;*

Eggplant: *Phomopsis vexans;*

Rape: *Alternaria japonica* and *Cercosporella brassicae;*

Welsh onion: *Puccinia allii;*

Soybean: *Cercospora kikuchii* and *Elsinoe glycines;*

Kidney bean: *Collectotrichum lindemuthianum;*

Peanut: *Mycosphaerella personatum* and *Cercospora arachidicola;*

Pea: *Erysiphe pisi;*

Potato: *Alternaria solani;*

Sugar beet: *Cercospora beticola;*

Rose: *Diplocarpon rosae* and *Sphaerotheca pannosa;*

Crop plants: *Botrytis cinerea* and *Sclerotinia sclerotiorum.*

Diseases more controllable among the above are

Rice: *Pyricularia oryzae, Rhizoctonia solani,*

Barley and wheat: *Septoria tritici, Pseudocercosporella herpotrichoides,* and most controllable is *Pyricularia oryzae* against rice and *Pseudocercosporella herpotrichoides, Septoria tritici* against barley and wheat.

The pyridinylpyrimidine derivative (I) is typically prepared by the methods as shown below:

Procedure (a):

A pyridinylpyrimidine derivative of the formula:

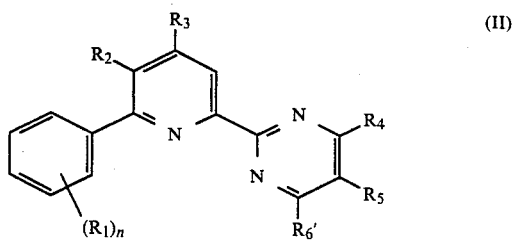
(II)

wherein $R_1$, $R_2$, $R_3$, $R_4$, $R_5$ and n are the same as defined above and $R_6'$ is hydrogen, is obtained by allowing a picoline amidine derivative of the formula:

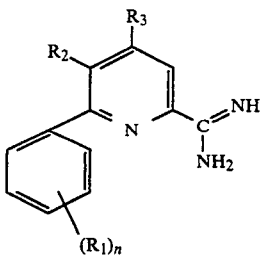

wherein $R_1$, $R_2$, $R_3$ and n are the same as defined above, or a salt thereof to react, in the presence of a base, with β-oxoacetal derivative of the formula:

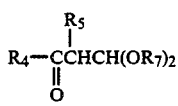

wherein $R_4$ and $R_5$ are the same as defined above and $R_7$ is lower alkyl such as $C_1$-$C_4$ alkyl.

Examples of the salt of picoline amidine derivative are hydrochloride, hydrobromide, acetate and formate. Examples of such base are alkali metal alkoxide such as sodium methoxide and sodium ethoxide and organic base such as triethylamine and N,N-diethylaniline. Sodium methoxide or sodium ethoxide is preferable.

The reaction is usually carried out in the presence of an inert solvent such as lower alcohol (e.g. methanol and ethanol), cyclic ether (e.g. dioxane and tetrahydrofuran), pyridine and N,N-dimethylformamide. The reaction may be carried out at 50°-150° C. for 1-6 hours.

The β-oxoacetal derivative (IV) and the base may be used in amounts of about 1 to 1.5 equivalents and about catalytic amount to 2.5 equivalents, respectively, to 1 equivalent of the picoline amidine derivative (III) or its salt.

After the reaction is lower, the reaction mixture is treated in a usual manner, such as concentration under reduced pressure, if necessary, chromatography to obtain the pyridinylpyrimidine derivative (II).

Procedure (b):

A pyridinylpyrimidine derivative (II) is obtained by reductive dehalogenation of a halopyrimidine derivative of the formula:

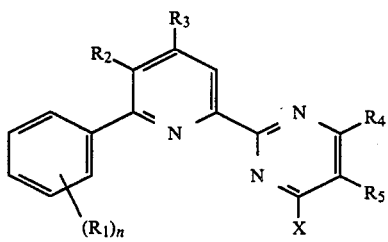

wherein $R_1$, $R_2$, $R_3$, $R_4$, $R_5$ and n are the same as defined above and X is halogen.

The dehalogenation is, for example, carried out in the presence of a catalyst such as palladium carbon, under hydrogen gas in an inert solvent such as water, lower alcohol (e.g. methanol or ethanol), ethylacetate, toluene or a mixture thereof.

In this procedure, it is preferable to use of hydrogen gas having a pressure of a range from 1 to 3 atom.

The procedure may be conducted in the presence of a dehydrohalogenating agent, such as a base (e.g., ammonia, sodium hydroxide, sodium carbonate, sodium acetate) or basic ion exchange resin (e.g., "Dowex"® (a product of Dow Chemical Co.)).

The reaction may be carried out at room temperature to 50° C. for 0.5-3 hours.

After the reaction is over, the reaction mixture is filtered to remove the waste catalyst, and the filtrate is concentrated in vacuo to give a residue. Then, when no dehydrohalogenating agent is used, aqueous solution of an inorganic base is added to the residue and the mixture is extracted with an organic solvent, while, when the dehydrohalogenating agent is used, water is added to the residue and the mixture is extracted with an organic solvent.

Then, the extract obtained above is treated in a usual manner such as concentration and further, if necessary, chromatography.

Procedure (c):

A pyridinylpyrimidine derivative of the formula:

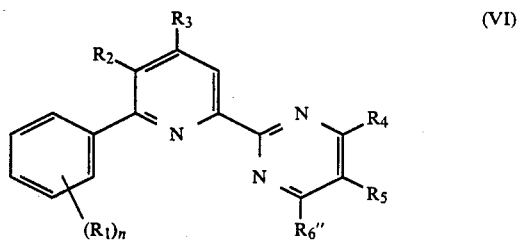

wherein $R_1$, $R_2$, $R_3$, $R_4$, $R_5$ and n are the same as defined above and $R_6''$ is lower alkoxy or lower alkylthio, is obtained by allowing the halopyrimidine derivative (V) to react with an alkali metal compound of the formula:

wherein $R_6''$ is defined above and Y is alkali metal.

Examples of the alkali metal are sodium, potassium, etc.

The reaction may be carried out at 10°-120° C. for 1 to 48 hours.

The alkali metal compound (VII) is usually used in an amount of about 1 to 1.5 equivalents to 1 equivalent of the halopyrimidine derivative (V).

The reaction is usually carried out in the presence of a solvent such as an alcohol, an ether and a mixture thereof.

In case of using the alkali metal compound wherein $R_6''$ is lower alkoxy, the corresponding alcohol to $R_6''$ moiety (e.g., methanol or ethanol), ether (e.g. diethyl ether, dioxane or tetrahydrofuran) or a mixture thereof is used as the solvent. In case of using the alkali metal compound wherein $R_6''$ is lower alkylthio, ether (e.g. diethylether, dioxane or tetrahydrofuran), nitrile (e.g. acetonitrile), aromatic hydrocarbon (e.g. toluene) water or a mixture thereof is used as the solvent.

After the reaction is over, the reaction mixture is concentrated in vacuo. The residue obtained is subjected to a usual post-treatment such as extraction with organic solvent, concentration, and if necessary, chromatography to obtain the objective compound (VI).

Procedure (d):

A pyridinylpyrimidine derivative of the formula:

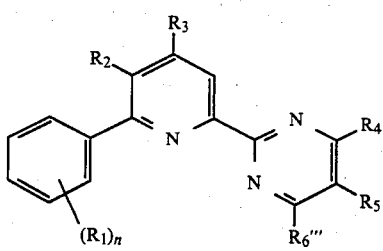

(VIII)

wherein $R_1, R_2, R_3, R_4, R_5$ and $n$ are the same as defined above and $R_6'''$ is lower alkyl, is obtained by allowing the halopyrimidine derivative (V) to react, in the presence of a base, with a diester derivative of the formula:

$$R_8CH(COOR_9)_2 \qquad (IV)$$

wherein $R_8$ is hydrogen, methyl or ethyl and $R_9$ is lower alkyl, followed by hydrolysis and decarbonation.

Examples of the base are alkali metal hydride (e.g. sodium hydride), alkyl lithium (e.g. n-butyl lithium), lithium dialkylamide (e.g. lithium diisopropylamide (LDA)) and alkali metal hydroxide (e.g. sodium hydroxide).

The reaction may be carried out at 0°–150° C. for 0.5–24 hours.

The diester derivative (IX) and the base are usually used in amounts of 1 to 2 equivalents, respectively, to 1 equivalent of the halopyrimidine derivative (V).

The reaction is usually carried out in the presence of an inert solvent (e.g. nitriles such as acetonitrile; ethers such as diethylether or tetrahydrofuran; halohydrocarbons such as chloroform; aromatic hydrocarbons such as benzene or toluene; haloaromatic hydrocarbons such as chlorobenzene; ketones such as acetone or methylisobutyl ketone; esters such as ethylacetate; sulfur compounds such as dimethylsulfoxide and sulfolane or mixture thereof).

After the reaction is over, the reaction mixture is subjected to a hydrolysis reaction and a decarbonation reaction to obtain the pyridinylpyrimidine derivative (VIII). The hydrolysis and the decarbonation are typically carried out in the manner as shown below.

To the reaction mixture is added 2.1 to 5 equivalents of the base to 1 equivalent of the halopyrimidine derivative (V) in the form of an aqueous solution or an aqueous lower alcohol (e.g. methanol or ethanol) solution at 10°–100° C. for a period from 10 minutes to 24 hours. Examples of the base are alkali metal hydroxide (e.g. sodium hydroxide) and alkali metal carbonate (e.g. sodium carbonate).

Into the reaction mixture obtained above is added 2.5 to 6 equivalents of acid to 1 equivalent of the used halopyrimidine derivative (V) for the decarbonation reaction. The decarbonation reaction may be carried out at 20°–150° C. for a period from 10 minutes to 24 hours.

Examples of the acid are inorganic acid such as sulfuric acid or hydrochloric acid and organic acid such as acetic acid.

After the reaction is over, the reaction mixture is firstly neutralized with alkali metal hydroxide such as sodium hydroxide, alkaline earth metal hydroxide such as calcium hydroxide, alkali metal carbonate such as sodium carbonate or sodium bicarbonate, or organic base such as triethylamine.

Then, the reaction mixture is treated in a usual manner such as concentration and extraction, if necessary, recrystallization and column chromatography to obtain the pyridinylpyrimidine derivative (VIII).

Procedure (e):

A pyridinylpyrimidine derivative of the formula:

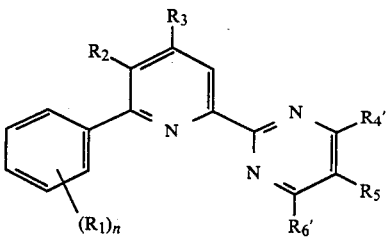

(X)

wherein $R_1, R_2, R_3, R_5$ and $n$ are the same as defined above and $R_4'$ and $R_6'$ are each hydrogen, is obtained by allowing a picoline amidine derivative (III) or a salt thereof, to react with acetal derivative of the formula:

$$(R_{10}O)_2CHCH\overset{R_5}{\underset{|}{C}}H(OR_{10})_2 \qquad (XI)$$

wherein $R_{10}$ is lower alkyl.

The reaction may be carried out at 50°–150° C. for 1–6 hours, in the absence of a solvent.

The acetal derivative (XI) may be used in an amount of about 1 to 3 equivalents to 1 equivalent of the picoline amidine derivative (III) or a salt thereof.

After the reaction is over, the reaction mixture is treated in a usual manner, such as concentration under reduced pressure, if necessary, chromatography to obtain the pyridinylpyrimidine derivative (X).

When $R_5$ and $R_6$ in the formula (I) are halogen and hydrogen, respectively, the present compound having the formula (I) is obtained by a method disclosed in "Synthesis", March 1984, pp. 253–4.

The present compound having the formula (I) is easily converted to salts thereof by allowing the compound to react with strong acid such as hydrochloric acid, hydrobromic acid, sulfuric acid or nitric acid.

The salt is typically obtained by the procedures shown below. The compound of the formula (I) is dissolved in a solvent and then one equivalent of the acid in the form of gas or aqueous solution is added thereto under ice cooling or at room temperature. After being left to stand for 10 minutes to one hour, the solution is subjected to a post-treatment such as concentration under reduced pressure, and if necessary recrystallization. Examples of the solvent are lower alcohol such as methanol or ethanol; aromatic hydrocarbon such as toluene or benzene; ether such as ethyl ether, tetrahydrofuran or dioxane; halogenated hydrocarbon such as chloroform; ketone such as acetone; ester such as ethyl acetate; hydrocarbon such as hexane; water or a mixture thereof.

Picoline amidine derivative of the formula (III) and halopyrimidine derivative of the formula (V) are typically prepared by the following reaction scheme:

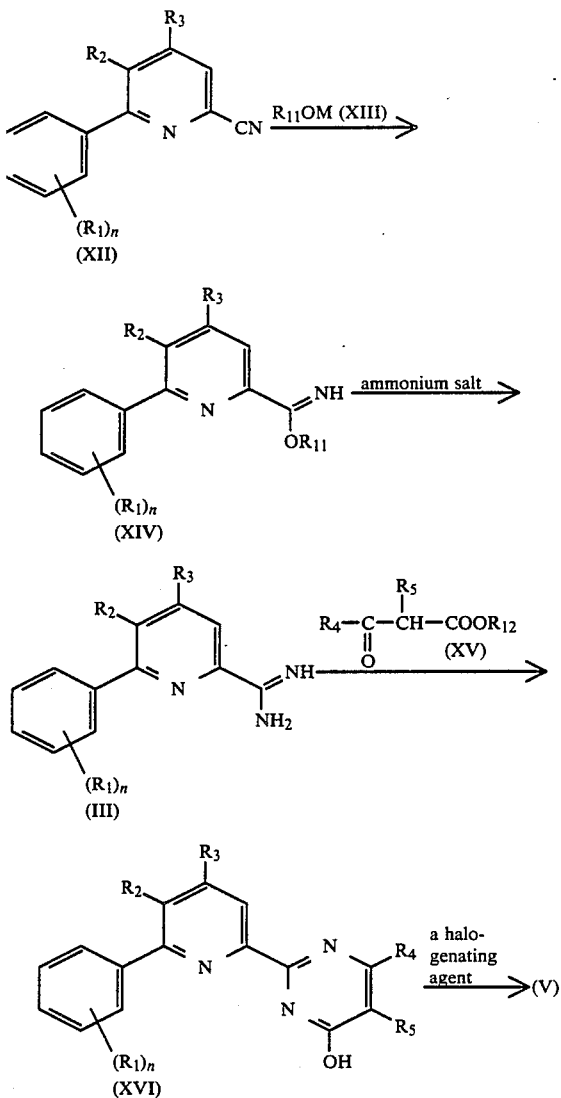

wherein $R_1$, $R_2$, $R_3$, $R_4$, $R_5$ and n are the same as defined above, $R_{11}$ and $R_{12}$ each represent lower alkyl and M is alkali metal.

An imidate derivative of the formula (XIV) is prepared by allowing a cyanopyridine derivative of the formula (XII), which is prepared by a method described in J. Org. Chem., 48, 1375–1377 (1983), to react with an alkoxide of the formula (XIII). The picoline amidine of the formula (III) is prepared by allowing the imidate derivative of the formula (XIV) to react with an ammonium salt, followed by the decomposition of a salt of the amidine derivative of the formula (III) obtained. A hydroxypyrimidine derivative of the formula (XVI) is obtained by allowing the picoline amidine derivative of the formula (III) or a salt thereof to react, in the presence of a base, with a β-oxocarboxylate of the formula (XV). The halopyrimidine derivative of the formula (V) is obtained by allowing the hydroxypyrimidine derivative of the formula (XVI) to react with a halogenating agent.

Details of the above production are as follows.
A reaction between the compound of the formula (XII) and the compound of the formula (XIII):
Examples of alkali metal atom in the alkoxide (XIII) are a sodium atom, a potassium atom, etc. The reaction is usually carried out in the presence of a solvent at 10° to 50° C. for 1 to 48 hours. The alkoxide (XIII) may be used in an amount of 0.1 to 1 equivalent to 1 equivalent of the cyanopilidine derivative (XII). As the solvent, there may be used, for example, a lower alcohol corresponding to $R_{11}$ of the alkoxide (XIII), (e.g. methyl alcohol, ethyl alcohol, n-propyl alcohol, isopropyl alcohol or n-butyl alcohol), preferably methyl alcohol or ethyl alcohol.

After the reaction is over, neutralization of the solution is effected with acid, concentrated under reduced pressure and dissoved in an organic solvent. After insoluble alkali metal salt is filtered out, the filtrate is concentrated in vacuo, and, if necessary, distilled to obtain the imidate derivative (XIV).

A reaction between the compound (XIV) and ammonium salt:

In the step, ammonium salt used is that of, for example, hydrochloric acid, hydrobromic acid, acetic acid or formic acid.

The reaction is usually carried out in the presence of a solvent at 30°–100° C. for 0.5–5 hour. The ammonium salt may be used in amounts of 1 to 1.1 equivalents to 1 equivalent of the imidate derivative (XIV). As the solvent, there may be used, for instance, a lower alcohol, preferably a solution of ethanol or water.

After the reaction is over, the reaction mixture may be concentrated in vacuo and, if necessary recrystalized to obtain such salt as hydrochloride, hydrobromide, acetate or formate of picoline amidine derivative of the formula (III). The salt is decomposed by a usual manner such as neutralization with an inorganic base, for example sodium hydroxide, potassium hydroxide, sodium methoxide of sodium ethoxide, to obtain picoline amidine derivative of the formula (III).

Alternatively, the salt may be subjected, as it is, to the next step where decomposition thereof is effected.

Reaction between picoline amidine derivative having the formula (III) or a salt thereof and the β-oxocarboxylate having the formula (XV):

The reaction is usually carried out in the presence of a solvent at 50°–150° C. for 1–24 hours. The β-oxocarboxylate (XV) may be used in an amount of 1 to 1.5 equivalents to 1 equivalent of the picoline amidine derivative (III) or a salt thereof. The base may be used from a catalytic amount to 1.5 equivalents to 1 equivalent of the picoline amidine derivative (III) or a salt thereof.

As the solvent, there may be used, for instance, lower alcohol such as methanol or ethanol, cyclic ether such as dioxane, tetrahydrofuran, pyridine, N,N-dimethylformamide, water or a mixture thereof.

As the base, there may be used, for instance, inorganic base such as sodium hydroxide, potassium hydroxide, potassium carbonate, or organic one such as alkali metal alkoxide such as sodium methoxide, triethylamine or N,N-diethylaniline. After the reaction is over, in case of using the salt of picoline amidine derivative of the formula (III), the by-produced inorganic salt is filtered out, and the filtrate is concentrated in vacuo to obtain a residue. The residue may be treated by chromatography or recrystallization to obtain the hydroxypyrimidine derivative (XVI).

Reaction between the hydroxypyrimidine derivative having the formula (XVI) and the halogenating agent:

As the halogenating agent, there may be used, for instance, thionyl chloride, phosgene, phosphoryl chloride, phosphorus pentachloride, phosphoryl bromide or phosphorus tribromide.

The reaction is usually carried out in the presence of a solvent at 50°–150° C. for 1–10 hours. The halogenating agent may be used in an amount of 1 to 10 equivalents to 1 equivalent of the hydroxypyrimidine derivative (XVI). As the solvent, there may be used, for instance, aromatic hydrocarbons (e.g. benzene or toluene), halogenated hydrocarbons (e.g. chlorobenzene), etc.

After the reaction is over, a post-treatment of the reaction mixture may be carried out in a usual manner. For instance, the reaction mixture is concentrated under reduced pressure and neutralized with an inorganic base (e.g. sodium hydroxide). Then, the above mixture is extracted with an organic solvent and the extract is concentrated in vacuo to obtain the halopyrimidine derivative (V). Any further procedure such as chromatography or recrystallization may be applied, if necessary, to the resultant product.

The pyridinyl pyrimidine derivatives of this invention may be used as an active ingredient of a plant disease protectant, and it is usually mixed with a solid carrier, a liquid carrier, a surface active agent, and other adjuvants and formulated into emulsion, wettable powder, suspension, granule, dust, or liquid.

These formulations may contain the pyridinylpyrimidine derivative in a concentration of about 0.1 to 99% by weight, preferably about 0.2 to 95% by weight.

Examples of solid carriers include kaolin clay, attapulgite clay, bentonite, Japanese acid clay, pyrophyllite, talc, diatomaceous earth, calcite, corncob powder, walnut shell powder, urea, ammonium sulfate, and synthetic hydrated silica, which are in the form of finely divided powder or granule. Examples of liquid carrier include aromatic hydrocarbons, e.g., xylene and methylnaphthalane; alcohols, e.g., isopropanol, ethylene glycol, and cellosolve; ketones, e.g., acetone, cyclohexanone, and isophorone; vegetable oils e.g., soybean oil and cottonseed oil; dimethylsulfoxide, acetonitrile or water.

Examples of surface active agents for emulsification, dispersion, and wetting include anionic surface active agents such as alkyl sulfate salt, alkyl or aryl sulfonate, dialkylsulfosuccinate, polyoxyethylene alkylarylether, phosphate salt, and naphthalene sulfonic acid-formalin condensate; and nonionic surface active agents such as polyoxyethylene alkyl ether, polyoxyethylene-polyoxypropylene block copolymer, sorbitan-fatty acid ester or polyoxyethylene-sorbitan fatty acid ester. Examples of adjuvants include ligninsulfonate, alginate, polyvinyl alcohol, gum arabic, CMC (carboxymethylcellulose) or PAP (isopropyl acidphosphate).

These formulations are used as such or after dilution with water for foliage application or soil treatment or soil incorporation. They may also be used in combination with other plant disease protectants for their enhanced control effect. Further, they may be used in combination with an insecticide, acaricide, nematicide, herbicide, plant growth regulator, fertilizer, and soil conditioner.

In the case where the present compound is used as an active ingredient of a plant disease protectant, the dosage varies depending on the weather conditions, formulation, application time, application method, application place, object diseases, and object crops. The dosage is usually 0.2 to 200 g, preferably 1 to 100 g for an area of 1 are. In the case of emulsion, wettable powder, suspension, or liquid formulation which is diluted with water prior to application, the concentration should be 0.005 to 0.5%, preferably 0.01 to 0.2% by weight. Granules and dusts are used as such without dilution.

The present invention is explained in further detail referring to synthesis examples, formulation examples and efficiency tests.

SYNTHESIS EXAMPLES OF THE PRESENT COMPOUND

Example 1

To the mixture of 6-m-chlorophenyl-2-picoline amidine hydrochloride (1 g) and methanol (50 ml) were added 28% sodium methoxide solution in methanol (1.08 g) and 1,1-dimethoxy-3-butanone (purity 90%, 0.7 g). The mixture was heated under refluxing for an hour, and was left to stand at room temperature. After the insoluble salt was filtered off, the reaction solution was concentrated under reduced pressure.

The residue obtained was subjected to silica gel column chromatography (eluent; n-hexane:acetone=2:1 in volume) to obtain 2-(6-chlorophenyl-2-pyridinyl)-4-methyl pyrimidine (0.86 g, yield 82%).

$n_D^{23}$ 1.6363.

PMR (CDCl$_3$) δppm: 2.60 (s, 3H, —CH$_3$) 7.06 (d, 1H, pyrimidine-H$^5$, J=5.4 Hz), 8.67 (d, 1H, pyrimidine-H$^6$, J=5.4 Hz).

EXAMPLE 2

To a solution of 4-chloro-6-methyl-2-(5-methyl-6-phenyl-2-pyridinyl)pyrimidine (1 g) in toluene (10 ml) and ethylalcohol (5 ml), were added a sodium carbonate (0.25 g) solution in water (2 ml), and then 5% palladium carbon (0.1 g).

The mixture was brought into contact with hydrogen gas for 30 minutes. After palladium carbon was filtered off, water (20 ml) was added and then extracted with toluene (30 ml). After the extract was dried over anhydrous magnesium sulfate, it was concentrated under reduced pressure to obtain 4-methyl-2-(5-methyl-6-phenyl-2-pyridinyl)pyrimidine (0.85 g, yield 96%)

m.p. 104.8° C.

PMR (CDCl$_3$) δppm: 2.36 (s, 3H, —CH$_3$), 2.59 (s, 3H, —CH$_3$), 7.05 (d, 1H, pyrimidine-H$^5$, J=5.4 Hz), 8.28 (d, 1H, pyridine-H$^3$, J=7.2 Hz), 8.67 (d, 1H, pyrimidine-H$^6$, J=5.4 Hz).

EXAMPLE 3

To 4-chloro-6-methyl-2-(6-o-tolyl-2-pyridinyl)pyrimidine (2 g) was added sodium methoxide prepared from methanol (10 ml) and metallic sodium (0.19 g). After the mixture was left to stand at room temperature for 30 minutes, water (30 ml) and chloroform (100 ml) was added thereto, and then extracted. After the extract was dried over anhydrous magnesium sulfate, it was concentrated under reduced pressure to obtain 4-methoxy-6-methyl-2-(6-o-tolyl-2-pyridinyl)pyrimidine (1.9 g, yield 96%).

m.p. 102.8° C.

PMR (CDCl$_3$) δppm: 2.51 (s, 6H, —CH$_3$), 4.03 (s, 3H, —OCH$_3$), 6.51 (s, 1H, pyrimidine-H$^5$), 7.79 (t, 1H, pyridine-H$^4$, J=7.2 Hz), 8.34 (d, 1H, pyridine-H$^3$, J=7.2 Hz).

EXAMPLE 4

To tetrahydrofuran (30 ml) were added diethylmalonate (1.6 g) and 60% oily sodium hydride (0.4 g), and then 4-chloro-6-methyl-2-(6-phenyl-2-pyridinyl)pyrimidine (2 g). The mixture was heated under refluxing for 30 minutes. Sodium hydroxide (0.85 g) solution in water (10 ml) and methanol (10 ml) was added thereto, and the mixture was further heated under refluxing for 20 minutes. After the mixture was left to stand until it was cooled to room temperature, sulfuric acid (1.4 g) was added dropwise thereto. The mixture was heated under refluxing for 30 minutes and left to stand to room temperature. 1-N aqueous sodium carbonate solution was added until a mixture was neutralized, and concentrated under reduced pressure. The residue was subjected to silica-gel column chromatography (eluent; n-hexane:acetone=3:1 in volume) to give 4,6-dimethyl-2-(6-phenyl-2-pyridinyl)pyrimidine (1.6 g, yield 86%).

m.p. 117.0° C.

PMR (CDCl$_3$) δppm: 2.53 (s, 6H,, —CH$_3$), 6.92 (s, 1H, pyrimidine-H$^5$).

EXAMPLE 5

To 6-phenyl-2-picoline amidine hydrochloride (1 g) was added malonaldehyde bis(dimethylacetal) (2.1 g).

The mixture was heated about 120° C. for an hour, and then concentrated under reduced pressure.

The residue obtained was subjected to silica gel column chromatography (eluent; n-hexane:acetone=1:1 in volume) to obtain 2-(6-phenyl-2-pyridinyl)pyrimidine (0.7 g, yield 70%).

PMR (CDCl$_3$) δppm: 7.11 (t, 1H, pyrimidine-H$^5$, J=4.8 Hz), 8.76 (d, 2H, pyrimidine-H$^4$ and H$^6$, J=4.8 Hz).

Some of compounds of this invention which are prepared according to the similar procedures to the above are listed in Table 1.

TABLE 1

Pyridinylpyrimidine derivatives or salts thereof

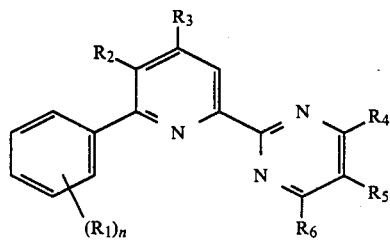

| Compound number | (R$_1$)$_n$ | R$_2$ | R$_3$ | R$_4$ | R$_5$ | R$_6$ | Physical constant |
|---|---|---|---|---|---|---|---|
| (1) | phenyl | H | H | H | H | H | m.p. 132.1° C. |
| (2) | phenyl | H | H | CH$_3$ | H | OCH$_3$ | m.p. 123.9° C. |
| (3) | phenyl | H | H | CH$_3$ | H | OC$_2$H$_5$ | n$_D^{28}$ 1.6185 |
| (4) | phenyl | H | H | CH$_3$ | H | CH$_3$ | m.p. 117.0° C. |
| (5) | phenyl | H | H | CH$_3$ | H | C$_2$H$_5$ | m.p. 90.2° C. |
| (6) | phenyl | H | H | CH$_3$ | H | H | m.p. 62.5° C. |

TABLE 1-continued
Pyridinylpyrimidine derivatives or salts thereof
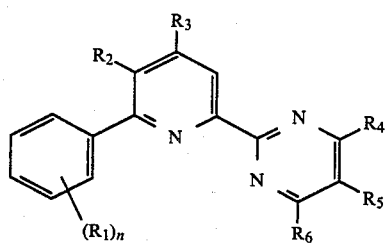
| Compound number | (R₁)ₙ | R₂ | R₃ | R₄ | R₅ | R₆ | Physical constant |
|---|---|---|---|---|---|---|---|
| (7) | ⌬- | H | H | $CH_3$ | H | $SCH_3$ | $n_D^{25}$ 1.6566 |
| (8) | ⌬- | H | H | $CH_3$ | $CH_3$ | $OCH_3$ | m.p. 126.0° C. |
| (9) | ⌬- | H | H | $CH_3$ | $CH_3$ | H | $n_D^{25.5}$ 1.6232 |
| (10) | ⌬- | H | H | $n\text{-}C_3H_7$ | H | $OCH_3$ | $n_D^{24}$ 1.6072 |
| (11) | ⌬- | H | H | $n\text{-}C_3H_7$ | H | H | $n_D^{27.5}$ 1.6107 |
| (12) | ⌬- | H | H | $-(CH_2)_4-$ | | $OCH_3$ | m.p. 127.4° C. |
| (13) | ⌬- | H | H | $-(CH_2)_4-$ | | H | m.p. 130.4° C. |
| (14) | ⌬- | $CH_3$ | H | $CH_3$ | H | $OCH_3$ | m.p. 89.3° C. |
| (15) | ⌬- | $CH_3$ | H | $CH_3$ | H | H | m.p. 104.8° C. |
| (16) | ⌬- | $CH_3$ | H | $CH_3$ | $CH_3$ | $OCH_3$ | m.p. 150.6° C. |

TABLE 1-continued
Pyridinylpyrimidine derivatives or salts thereof
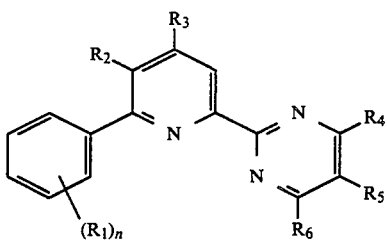
| Compound number | (R₁)ₙ | R₂ | R₃ | R₄ | R₅ | R₆ | Physical constant |
|---|---|---|---|---|---|---|---|
| (17) | phenyl | CH₃ | H | CH₃ | CH₃ | CH₃ | m.p. 155.7° C. |
| (18) | phenyl | CH₃ | H | CH₃ | CH₃ | H | m.p. 163.0° C. |
| (19) | phenyl | H | t-C₄H₉ | CH₃ | H | H | m.p. 106.1° C. |
| (20) | 2-CH₃-phenyl | H | H | CH₃ | H | OCH₃ | m.p. 102.8° C. |
| (21) | 2,6-(CH₃)₂-phenyl | H | H | CH₃ | H | OC₂H₅ | $n_D^{23}$ 1.5883 |
| (22) | 2-CH₃-phenyl | H | H | CH₃ | H | CH₃ | $n_D^{23}$ 1.6055 |
| (23) | 2-CH₃-phenyl | H | H | CH₃ | H | H | $n_D^{25}$ 1.6129 |
| (24) | 2-CH₃-phenyl | CH₃ | H | H | H | H | m.p. 129.4° C. |

TABLE 1-continued
Pyridinylpyrimidine derivatives or salts thereof
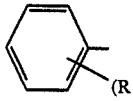
| Compound number | (R₁)ₙ | R₂ | R₃ | R₄ | R₅ | R₆ | Physical constant |
|---|---|---|---|---|---|---|---|
| (25) | 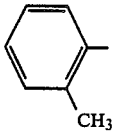 2,3-(CH₃)₂ | $CH_3$ | H | $CH_3$ | H | H | m.p. 81.0° C. |
| (26) | 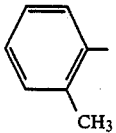 2,3-(CH₃)₂ | H | $CH_3$ | $CH_3$ | H | $OCH_3$ | m.p. 119.6° C. |
| (27) | 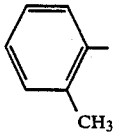 2,3-(CH₃)₂ | H | $CH_3$ | $CH_3$ | H | H | $n_D^{27.5}$ 1.5928 |
| (28) | 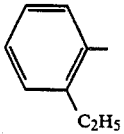 2-C₂H₅ | H | H | $CH_3$ | H | $OCH_3$ | $n_D^{24}$ 1.6031 |
| (29) | 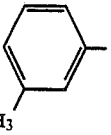 3-CH₃ | H | H | $CH_3$ | H | $OCH_3$ | $n_D^{25}$ 1.5823 |
| (30) | 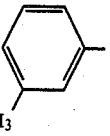 3-CH₃ | H | H | $CH_3$ | H | $CH_3$ | m.p. 138.2° C. |
| (31) | 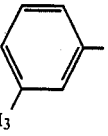 3-CH₃ | H | H | $CH_3$ | H | H | $n_D^{25.5}$ 1.6360 |
| (32) |  4-CH₃ | H | H | $CH_3$ | H | $OCH_3$ | m.p. 127.6° C. |

TABLE 1-continued
Pyridinylpyrimidine derivatives or salts thereof
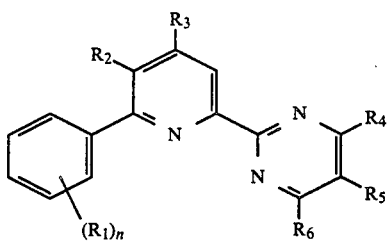
| Compound number | (R₁)ₙ (aryl) | R₂ | R₃ | R₄ | R₅ | R₆ | Physical constant |
|---|---|---|---|---|---|---|---|
| (33) | 4-CH₃-C₆H₄- | H | H | CH₃ | H | CH₃ | m.p. 156.1° C. |
| (34) | 4-CH₃-C₆H₄- | H | H | CH₃ | H | H | m.p. 132.0° C. |
| (35) | 4-CH₃-C₆H₄- | CH₃ | H | H | H | H | m.p. 144.6° C. |
| (36) | 4-CH₃-C₆H₄- | CH₃ | H | CH₃ | H | H | m.p. 153.8° C. |
| (37) | 2,4-(CH₃)₂-C₆H₃- | H | H | H | H | H | $n_D^{25}$ 1.6167 |
| (38) | 2,4-(CH₃)₂-C₆H₃- | H | H | CH₃ | H | OCH₃ | $n_D^{24}$ 1.5862 |
| (39) | 2,4-(CH₃)₂-C₆H₃- | H | H | CH₃ | H | H | $n_D^{27.5}$ 1.6049 |
| (40) | 2,3-(CH₃)₂-C₆H₃- | H | H | H | H | H | m.p. 138.6° C. |

TABLE 1-continued
Pyridinylpyrimidine derivatives or salts thereof

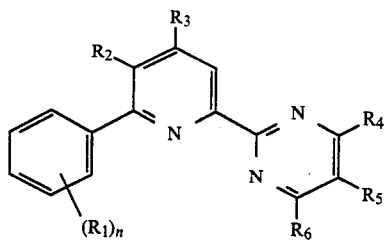

| Compound number | (R₁)n | R₂ | R₃ | R₄ | R₅ | R₆ | Physical constant |
|---|---|---|---|---|---|---|---|
| (41) | 2,6-(CH₃)₂-phenyl | CH₃ | H | H | CH₃ | H | OCH₃ | m.p. 119.1° C. |
| (42) | 2,6-(CH₃)₂-phenyl | CH₃ | H | H | CH₃ | H | CH₃ | m.p. 129.0° C. |
| (43) | 2,6-(CH₃)₂-phenyl | CH₃ | H | H | CH₃ | H | H | m.p. 129.1° C. |
| (44) | 2,4,6-(CH₃)₃-phenyl | CH₃ | H | H | H | H | H | m.p. 120.8° C. |
| (45) | 2,4,6-(CH₃)₃-phenyl | CH₃ | H | H | CH₃ | H | H | m.p. 142.5° C. |
| (46) | 2-Cl-phenyl | | H | H | CH₃ | H | OCH₃ | m.p. 123.9° C. |
| (47) | 2-Cl-phenyl | | H | H | CH₃ | H | CH₃ | $n_D^{25}$ 1.6010 |

Note: For compounds (41)-(45) the (R₁)n substituent is drawn as a substituted phenyl ring; the R₂ column value (CH₃) is the first column of data. The table as rendered has R₂ = CH₃ for (41)-(45), R₃ = H, R₄ as listed, R₅ = H, R₆ as listed.

TABLE 1-continued
Pyridinylpyrimidine derivatives or salts thereof

| Compound number | (R₁)ₙ [phenyl] | R₂ | R₃ | R₄ | R₅ | R₆ | Physical constant |
|---|---|---|---|---|---|---|---|
| (48) | 2-Cl-phenyl | H | H | CH₃ | H | H | m.p. 116.2° C. |
| (49) | 2-Cl-phenyl | CH₃ | H | H | H | H | m.p. 128.7° C. |
| (50) | 2-Cl-phenyl | CH₃ | H | CH₃ | H | H | m.p. 114.9° C. |
| (51) | 2-Cl-phenyl | H | CH₃ | CH₃ | H | H | m.p. 84.2° C. |
| (52) | 2-Cl-phenyl | H | CH₃ | CH₃ | CH₃ | H | $n_D^{17}$ 1.6054 |
| (53) | 2-Cl-phenyl | H | CH₃ | CH₃ | Cl | H | m.p. 106.4° C. |
| (54) | 3-Cl-phenyl | H | H | CH₃ | H | CH₃ | m.p. 138.7° C. |
| (55) | 3-Cl-phenyl | H | H | CH₃ | H | H | $n_D^{23}$ 1.6363 |

TABLE 1-continued
Pyridinylpyrimidine derivatives or salts thereof
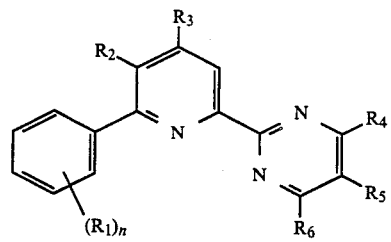
| Compound number | (R₁)ₙ | R₂ | R₃ | R₄ | R₅ | R₆ | Physical constant |
|---|---|---|---|---|---|---|---|
| (56) | 4-Cl-phenyl | H | H | CH₃ | H | OCH₃ | m.p. 114.0° C. |
| (57) | 4-Cl-phenyl | H | H | CH₃ | H | CH₃ | m.p. 157.5° C. |
| (58) | 4-Cl-phenyl | H | H | CH₃ | H | H | m.p. 95.2° C. |
| (59) | 4-F-phenyl | H | H | CH₃ | H | OCH₃ | m.p. 63.7° C. |
| (60) | 4-F-phenyl | H | H | CH₃ | H | H | m.p. 169.3° C. |
| (61) | 3,5-diCl-phenyl | H | H | CH₃ | H | H | m.p. 138.1° C. |
| (62) | 2,6-diCl-phenyl | H | H | CH₃ | H | H | m.p. 145.5° C. |
| (63) | 2-CF₃-phenyl | H | H | CH₃ | H | OCH₃ | m.p. 91.8° C. |

TABLE 1-continued
Pyridinylpyrimidine derivatives or salts thereof
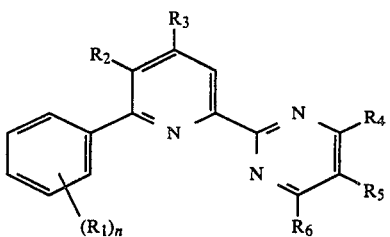
| Compound number | (R₁)ₙ | R₂ | R₃ | R₄ | R₅ | R₆ | Physical constant |
|---|---|---|---|---|---|---|---|
| (64) | 2-CF₃-phenyl | H | H | CH₃ | H | CH₃ | m.p. 104.1° C. |
| (65) | 2-CF₃-phenyl | H | H | CH₃ | H | H | m.p. 91.7° C. |
| (66) | 3-CF₃-phenyl | H | H | H | H | H | $n_D^{25}$ 1.5892 |
| (67) | 3-CF₃-phenyl | H | H | CH₃ | H | OCH₃ | $n_D^{29}$ 1.5862 |
| (68) | 3-CF₃-phenyl | H | H | CH₃ | H | C₂H₅ | $n_D^{24}$ 1.5478 |
| (69) | 3-CF₃-phenyl | H | H | CH₃ | H | H | $n_D^{29}$ 1.6768 |
| (70) | 2-OCH₃-phenyl | H | H | CH₃ | H | OCH₃ | $n_D^{24}$ 1.6092 |
| (71) | 2-OCH₃-phenyl | H | H | CH₃ | H | H | $n_D^{27.5}$ 1.6135 |

TABLE 1-continued
Pyridinylpyrimidine derivatives or salts thereof

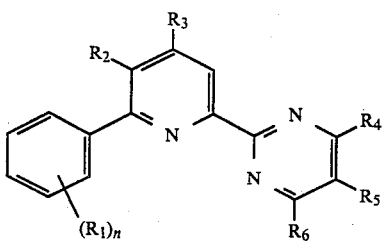

| Compound number | (R₁)ₙ ⌬ | R₂ | R₃ | R₄ | R₅ | R₆ | Physical constant |
|---|---|---|---|---|---|---|---|
| (72) | 3-F, 4-CH₃ phenyl | H | H | CH₃ | H | H | m.p. 81.2° C. |
| (73) | 3-F, 5-CH₃ phenyl | H | H | CH₃ | H | H | m.p. 108.3° C. |
| (74) | HCl salt of compound No. 6 | | | | | | m.p. 180.9° C. |
| (75) | ½·H₂SO₄ salt of compound No. 6 | | | | | | m.p. 179.1° C. |
| (76) | HNO₃ salt of compound No. 6 | | | | | | m.p. 120.5° C. |

The following reference examples show the preparation of various starting compounds.

REFERENCE EXAMPLE 1

Preparation of picoline amidine derivative (III) (HCl-salt)

2-Cyano-6-phenylpyridine (20 g) was dissolved in a solution of sodium methoxide in methanol prepared from methanol (200 ml) and metallic sodium (0.77 g). After the solution was left to stand overnight, acetic acid (2.0 g) was added thereto, followed by concentration under reduced pressure. The resulting residue was dissolved in ether (200 ml) and insoluble materials were filtered out. The filtrate was concentrated under reduced pressure to obtain methyl 2-picoline imidate.

To the imidate obtained above was added a solution of ammonium chloride (5.94 g) in water (30 ml) and ethanol (120 ml) and the mixture was heated under refluxing for one hour. After being left to stand to cool, the reaction mixture was concentrated under reduced pressure. The crystalline residue obtained was washed with acetone to obtain 6-phenyl-2-picoline amidine hydrochloride (22 g).
m.p. 166.5° C.

Some of picoline amidine derivatives or salts thereof having the formula (III) which are able to prepare according to the similar procedure to the above are listed in Table 2.

TABLE 2
Picoline amidine derivatives or their salts

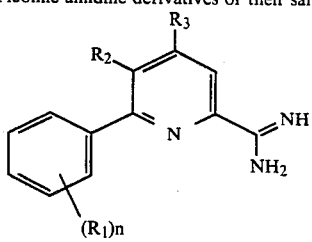

| (R₁)ₙ ⌬ | R₂ | R₃ | Physical constant |
|---|---|---|---|
| phenyl | H | H | m.p. 166.5° C. (HCl salt) |
| phenyl | CH₃ | H | m.p. 259.0° C. (HCl salt) |
| phenyl | H | t-C₄H₉ | m.p. 277.0° C. (HCl salt) |

TABLE 2-continued

Picoline amidine derivatives or their salts

| (R₁)n phenyl | R₂ | R₃ | Physical constant |
|---|---|---|---|
| 2-CH₃-phenyl | H | H | m.p. 194.0° C. |
| 3-CH₃-phenyl | H | H | m.p. 209.5° C. (HCl salt) |
| 2-CH₃-phenyl | CH₃ | H | m.p. 271.0° C. (HCl salt) |
| 2-CH₃-phenyl | H | CH₃ | m.p. 248.0° C. (HCl salt) |
| 2-C₂H₅-phenyl | H | H | m.p. 243.5° C. (HCl salt) |
| 3-CH₃-phenyl | H | H | m.p. 192.0° C. (HCl salt) |
| 4-CH₃-phenyl | H | H | m.p. 224.0° C. (HCl salt) |
| 4-CH₃-phenyl | CH₃ | H | m.p. 276.5° C. (HCl salt) |
| 2,4-(CH₃)₂-phenyl | H | H | m.p. 254.0° C. (HCl salt) |
| 2,6-(CH₃)₂-phenyl | H | H | m.p. 300° C. or more (HCl salt) |
| 2,4,6-(CH₃)₃-phenyl | H | H | m.p. 246.5° C. (HCl salt) |
| 2-Cl-phenyl | H | H | m.p. 246.1° C. (HCl salt) |
| 2-Cl-phenyl | CH₃ | H | m.p. 266.5° C. (HCl salt) |
| 2-Cl-phenyl | H | CH₃ | m.p. 237.0° C. (HCl salt) |
| 3-Cl-phenyl | H | H | m.p. 169.8° C. (HCl salt) |
| 4-Cl-phenyl | H | H | m.p. 266.6° C. (HCl salt) |

TABLE 2-continued

Picoline amidine derivatives or their salts

| (R₁)n | R₂ | R₃ | Physical constant |
|---|---|---|---|
| 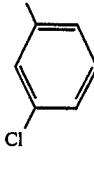 2,4-diCl | H | H | m.p. 255.5° C. (HCl salt) |
| 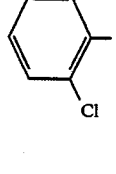 2,6-diCl | H | H | m.p. 248.2° C. (HCl salt) |
| 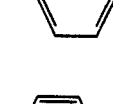 4-F | H | H | m.p. 122.8° C. (HCl salt) |
| 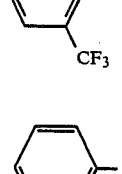 2-CF₃ | H | H | m.p. 290.9° C. (HCl salt) |
| 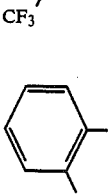 3-CF₃ | H | H | m.p. 180.7° C. (HCl salt) |
| 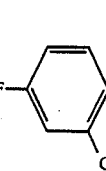 2-OCH₃ | H | H | m.p. 181.5° C. (HCl salt) |
| 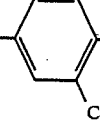 4-F, 3-CH₃ | H | H | m.p. 232.7° C. (HCl salt) |

TABLE 2-continued

Picoline amidine derivatives or their salts

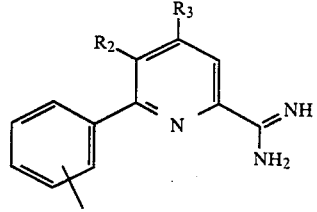

| (R₁)n | R₂ | R₃ | Physical constant |
|---|---|---|---|
| 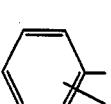 3-F, 4-CH₃ | H | H | m.p. 147.5° C. (HCl salt) |

REFERENCE EXAMPLE 2

Preparation of hydroxypyrimidine derivative (XVI)

6-Phenyl-2-picoline amidine hydrochloride (4 g) was dissolved in a solution of sodium ethoxide in ethanol prepared from ethanol (100 ml) and metallic sodium (0.47 g).

Ethyl acetoacetate (2.45 g) was added to the solution obtained above, then the mixture was heated under refluxing for 1 hour. After the reaction mixture was cooled to room temperature, it was neutralized with acetic acid and then concentrated under reduced pressure. The residue obtained was washed with water and n-hexane to obtain 4-hydroxy-6-methyl-2-(6-phenyl-2-pyridinyl)pyrimidine (3.96 g, yield 88%).

m.p. 172.2° C.

PMR (CDCl₃) δppm: 2.37 (s, 3H, —$\underline{CH_3}$), 6.29 (s, 1H, pyrimidine-H⁵).

Some of hydroxypyrimidine derivatives (XVI) according to the similar procedure to the above are listed in Table 3.

TABLE 3

Hydroxypyrimidine derivatives

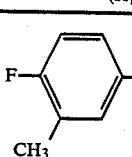

| (R₁)n | R₂ | R₃ | R₄ | R₅ | Physical constant |
|---|---|---|---|---|---|
| H | H | H | CH₃ | H | m.p. 172.2° C. |

TABLE 3-continued
Hydroxypyrimidine derivatives

| (R₁)n (aryl) | R₂ | R₃ | R₄ | R₅ | Physical constant |
|---|---|---|---|---|---|
| phenyl | H | H | CH₃ | CH₃ | m.p. 193.2° C. |
| phenyl | H | H | n-C₃H₇ | H | m.p. 203.0° C. |
| phenyl | H | H | –(CH₂)₄– | | m.p. 184.2° C. |
| phenyl | CH₃ | H | CH₃ | H | m.p. 183.6° C. |
| phenyl | CH₃ | H | CH₃ | CH₃ | m.p. 164.3° C. |
| 2-CH₃-phenyl | H | H | CH₃ | H | m.p. 173.1° C. |
| 2-CH₃-phenyl | H | CH₃ | CH₃ | H | m.p. 234.6° C. |
| 2-C₂H₅-phenyl | H | H | CH₃ | H | m.p. 114.3° C. |
| 3-CH₃-phenyl | H | H | CH₃ | H | m.p. 163.4° C. |
| 4-CH₃-phenyl | H | H | CH₃ | H | m.p. 258.0° C. |
| 3,4-(CH₃)₂-phenyl | H | H | CH₃ | H | m.p. 173.7° C. |
| 2,6-(CH₃)₂-phenyl | H | H | CH₃ | H | m.p. 164.5° C. |
| 2-Cl-phenyl | H | H | CH₃ | H | m.p. 219.0° C. |
| 2-Cl-phenyl | H | CH₃ | CH₃ | CH₃ | m.p. 128.4° C. |
| 2-Cl-phenyl | H | CH₃ | CH₃ | Cl | m.p. 139.0° C. |
| 3-Cl-phenyl | H | H | CH₃ | H | m.p. 189.6° C. |
| 4-F-phenyl | H | H | CH₃ | H | m.p. 231.0° C. |

TABLE 3-continued
Hydroxypyrimidine derivatives

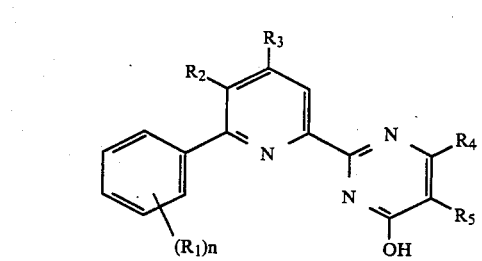

| (R₁)n | R₂ | R₃ | R₄ | R₅ | Physical constant |
|---|---|---|---|---|---|
| 2-CF₃-C₆H₄ | H | H | CH₃ | H | m.p. 184.1° C. |
| 3-CF₃-C₆H₄ | H | H | CH₃ | H | m.p. 222.5° C. |
| 2-OCH₃-C₆H₄ | H | H | CH₃ | H | m.p. 193.1° C. |

REFERENCE EXAMPLE 3

Preparation of halopyrimidine derivative (V)

To solution of 4-hydroxy-6-methyl-2-(6-m-tolyl-2-pyridinyl)pyrimidine (5 g) in toluene (100 ml), was added phosphoryl chloride (5 g). The mixture was heated under refluxing for one hour and left to stand to room temperature. Aqueous sodium carbonate solution was added thereto until the reaction solution became about pH 8 to be separated into two layers. Toluene layer was washed with water and dried over anhydrous magnesium sulfate. The toluene layer was concentrated under reduced pressure to obtain 4-chloro-6-methyl-2-(6-m-tolyl-2-pyridinyl)pyrimidine (4.9 g, yield 92%). m.p. 104.9° C.

PMR (CDCl₃) δppm: 2.44 (s, 3H, —CH₃), 2.63 (s, 3H, —CH₃).

Some of halopyrimidine derivatives (V) prepared according to the similar procedure to the above are listed in Table 4.

TABLE 4
Halopyrimidine derivatives

| (R₁)n | R₂ | R₃ | R₄ | R₅ | X | Physical constant |
|---|---|---|---|---|---|---|
| C₆H₅ | H | H | CH₃ | H | Cl | m.p. 103.4° C. |
| C₆H₅ | H | H | CH₃ | CH₃ | Cl | m.p. 123.4° C. |
| C₆H₅ | H | H | n-C₃H₇ | H | Cl | m.p. 81.3° C. |
| C₆H₅ | CH₃ | H | CH₃ | H | Cl | m.p. 128.5° C. |
| C₆H₅ | CH₃ | H | CH₃ | CH₃ | Cl | m.p. 155.3° C. |
| 3-CH₃-C₆H₄ | H | H | CH₃ | H | Cl | resin |
| 3-CH₃-C₆H₄ | H | CH₃ | CH₃ | H | Cl | m.p. 84.6° C. |
| 3-C₂H₅-C₆H₄ | H | H | CH₃ | H | Cl | $n_D^{24}$ 1.6103 |
| 3-CH₃-C₆H₄ | H | H | CH₃ | H | Cl | m.p. 104.9° C. |

TABLE 4-continued
Halopyrimidine derivatives

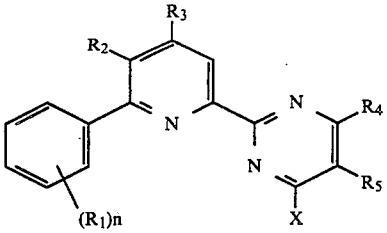

| (R₁)n | R₂ | R₃ | R₄ | R₅ | X | Physical constant |
|---|---|---|---|---|---|---|
| 4-CH₃-phenyl | H | H | CH₃ | H | Cl | m.p. 138.5° C. |
| 2,3-di-CH₃-phenyl | H | H | CH₃ | H | Cl | m.p. 60.7° C. |
| 2,6-di-CH₃-phenyl | H | H | CH₃ | H | Cl | m.p. 129.1° C. |
| 2-Cl-phenyl | H | H | CH₃ | H | Cl | $n_D^{29.5}$ 1.6768 |
| 2,3-di-Cl-phenyl | H | CH₃ | CH₃ | CH₃ | Cl | m.p. 130.1° C. |
| 2,3-di-Cl-phenyl | H | CH₃ | CH₃ | Cl | Cl | m.p. 170.7° C. |
| 3-Cl-phenyl | H | H | CH₃ | H | Cl | m.p. 107.7° C. |
| 4-Cl-phenyl | H | H | CH₃ | H | Cl | m.p. 151.0° C. |
| 4-F-phenyl | H | H | CH₃ | H | Cl | m.p. 121.0° C. |
| 2-CF₃-phenyl | H | H | CH₃ | H | Cl | m.p. 112.5° C. |
| 3-CF₃-phenyl | H | H | CH₃ | H | Cl | m.p. 101.8° C. |
| 2-OCH₃-phenyl | H | H | CH₃ | H | Cl | m.p. 119.5° C. |

FORMULATION EXAMPLES

The present compounds used are identified by numbers shown in Table 1. Quantities are expressed by parts by weight.

FORMULATION EXAMPLE 1

A wettable powder each is prepared by mixing and pulverizing 50 parts of each of the present compounds (1)-(76), 3 parts of calcium ligninsulfonate, 2 parts of sodium lauryl sulfate and 45 parts of synthetic hydrated silica.

FORMULATION EXAMPLE 2

A suspension each is prepared by mixing 25 parts of each of the present compounds (1)-(76), 3 parts of polyoxyethylene sorbitanmonooleate, 3 parts of CMC and 69 parts of water, followed by wet grinding to give a particle size smaller than 5 microns.

FORMULATION EXAMPLE 3

A dust each is prepared by mixing and pulverizing 2 parts of each of the present compounds (1)-(76), 88 parts of kaolin clay and 10 parts of talc.

FORMULATION EXAMPLE 4

An emulsifiable concentrate each is prepared by thoroughly mixing 20 parts of each of the present compounds (1)–(76), 14 parts of polyoxyethylene styrylphenyl ether, 6 parts of calcium dodecylbenzenesulfonate and 60 parts of xylene.

FORMULATION EXAMPLE 5

A granule each is prepared by mixing and pulverizing 2 parts of each of the present compounds (1)–(76), 1 part of synthetic hydrated silica, 2 parts of calcium ligninsulfonate, 30 parts of bentonite, and 65 parts of kaolin clay, followed by kneading with water, granulation and drying.

The following test examples demonstrate the effectiveness of the present compound used as an active ingredient of plant disease protectants. The present compounds used in the test examples are identified by the compound numbers shown in Table 1, and the compounds used for control are identified by the compound symbols shown in Table 5.

TABLE 5

| Compound symbol | Compound | Remarks |
|---|---|---|
| A | 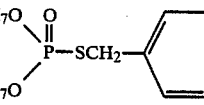 | Commercial fungicide "IBP" |
| B | — | Commerical fungicide "Validamycin" |
| C | 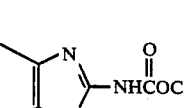 | Commerical fungicide "MBC" |
| D | 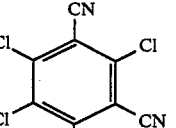 | Commerical fungicide "TPN" |
| E | 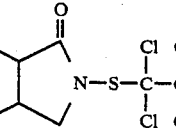 | Commerical fungicide "Captafol" |

The controlling effect was evaluated by visually observing the degree of fungus colony and infected area of the leaves and stems of the test plants. The results of evaluation were expressed in terms of six ratings as follows:

"5" Not observed at all.
"4" Observed on about 10% of the leaves and stems.
"3" Observed on about 30% of the leaves and stems.
"2" Observed on about 50% of the leaves and stems.
"1" Observed on about 70% of the leaves and stems.
"0" Same as control.

TEST EXAMPLE 1

Test for preventive controlling effect on blast (*Pyricularia oryzae*) of rice

Rice seeds (var.: Kinki No. 33) were sown in the sandy loam filled in a plastic pot. After raised for 20 days in a greenhouse, the seedlings were subjected to foliage application with a spray liquid of the wettable powder prepared according to Formulation Example 1 which was diluted with water to the given concentrations. After application, the seedlings were air-dried and then inoculated with spores of *Pyricularia oryzae* by spraying a suspension of spores. The inoculated seedlings were grown in a dark damp place at 28° C. for 4 days, and the controlling effect was examined. The results are shown in Table 6.

TABLE 6

| Compound No. | Concentration of active ingredient (ppm) | Control effect |
|---|---|---|
| Present compound | | |
| (1) | 200 | 5 |
| (2) | 200 | 5 |
| (3) | 200 | 5 |
| (4) | 200 | 5 |
| (5) | 200 | 5 |
| (6) | 200 | 5 |
| (7) | 200 | 5 |
| (8) | 200 | 5 |
| (9) | 200 | 5 |
| (10) | 200 | 5 |
| (11) | 200 | 5 |
| (12) | 200 | 5 |
| (13) | 200 | 5 |
| (14) | 200 | 5 |
| (15) | 200 | 5 |
| (16) | 200 | 5 |
| (17) | 200 | 5 |
| (18) | 200 | 5 |
| (19) | 200 | 5 |
| (20) | 200 | 5 |
| (21) | 200 | 5 |
| (22) | 200 | 5 |
| (23) | 200 | 5 |
| (24) | 200 | 5 |
| (25) | 200 | 5 |
| (26) | 200 | 5 |
| (27) | 200 | 5 |
| (28) | 200 | 5 |
| (29) | 200 | 5 |
| (30) | 200 | 5 |
| (31) | 200 | 5 |
| (32) | 200 | 5 |
| (33) | 200 | 5 |
| (34) | 200 | 5 |
| (35) | 200 | 5 |
| (36) | 200 | 5 |
| (37) | 200 | 5 |
| (38) | 200 | 5 |
| (39) | 200 | 5 |
| (40) | 200 | 5 |
| (41) | 200 | 5 |
| (42) | 200 | 5 |
| (43) | 200 | 5 |
| (44) | 200 | 5 |
| (45) | 200 | 5 |
| (46) | 200 | 5 |
| (47) | 200 | 5 |
| (48) | 200 | 5 |
| (49) | 200 | 5 |
| (50) | 200 | 5 |
| (51) | 200 | 5 |
| (52) | 200 | 5 |
| (53) | 200 | 5 |
| (54) | 200 | 5 |
| (55) | 200 | 5 |
| (56) | 200 | 5 |
| (57) | 200 | 5 |

TABLE 6-continued

| Compound No. | Concentration of active ingredient (ppm) | Control effect |
|---|---|---|
| (58) | 200 | 5 |
| (59) | 200 | 5 |
| (60) | 200 | 5 |
| (61) | 200 | 5 |
| (62) | 200 | 5 |
| (63) | 200 | 5 |
| (64) | 200 | 5 |
| (65) | 200 | 5 |
| (66) | 200 | 5 |
| (67) | 200 | 5 |
| (68) | 200 | 5 |
| (69) | 200 | 5 |
| (70) | 200 | 5 |
| (71) | 200 | 5 |
| (72) | 200 | 5 |
| (73) | 200 | 5 |
| (74) | 200 | 5 |
| (75) | 200 | 5 |
| (76) | 200 | 5 |
| Reference compound A | 200 | 4 |

TEST EXAMPLE 2

Test for curative controlling effect on blast (*Pyricularia oryzae*) of rice

Rice seeds (var.: Kinki No. 33) were sown in the sandy loam filled in a plastic pot. After raising for 20 days in a greenhouse, the seedlings were inoculated with spores of *Pyricularia oryzae* by spraying a suspension of spores. The inoculated seedlings were grown in a dark damp place at 28° C. for 16 hours. The seedlings were subjected to foliage application with a spray liquid of the emulsion prepared according to Formulation Example 4 which was diluted with water to the given concentrations. After application, the seedlings were grown in a dark damp place at 28° C. for 3 days, and the controlling effect was examined. The results are shown in Table 7.

TABLE 7

| Compound No. | Concentration of active ingredient (ppm) | Control effect |
|---|---|---|
| Present compound | | |
| (1) | 200 | 5 |
| (2) | 200 | 5 |
| (3) | 200 | 5 |
| (4) | 200 | 5 |
| (5) | 200 | 5 |
| (6) | 200 | 5 |
| (7) | 200 | 5 |
| (8) | 200 | 5 |
| (9) | 200 | 5 |
| (10) | 200 | 5 |
| (11) | 200 | 5 |
| (12) | 200 | 5 |
| (13) | 200 | 5 |
| (14) | 200 | 5 |
| (15) | 200 | 5 |
| (16) | 200 | 5 |
| (17) | 200 | 5 |
| (18) | 200 | 5 |
| (19) | 200 | 5 |
| (20) | 200 | 5 |
| (21) | 200 | 5 |
| (22) | 200 | 5 |
| (23) | 200 | 5 |
| (24) | 200 | 5 |
| (25) | 200 | 5 |
| (26) | 200 | 5 |
| (27) | 200 | 5 |
| (28) | 200 | 5 |
| (29) | 200 | 5 |

TABLE 7-continued

| Compound No. | Concentration of active ingredient (ppm) | Control effect |
|---|---|---|
| (30) | 200 | 5 |
| (31) | 200 | 5 |
| (32) | 200 | 5 |
| (33) | 200 | 5 |
| (34) | 200 | 5 |
| (35) | 200 | 5 |
| (36) | 200 | 5 |
| (37) | 200 | 5 |
| (38) | 200 | 5 |
| (39) | 200 | 5 |
| (40) | 200 | 5 |
| (41) | 200 | 5 |
| (42) | 200 | 5 |
| (43) | 200 | 5 |
| (44) | 200 | 5 |
| (45) | 200 | 5 |
| (46) | 200 | 5 |
| (47) | 200 | 5 |
| (48) | 200 | 5 |
| (49) | 200 | 5 |
| (50) | 200 | 5 |
| (51) | 200 | 5 |
| (52) | 200 | 5 |
| (53) | 200 | 5 |
| (54) | 200 | 5 |
| (55) | 200 | 5 |
| (56) | 200 | 5 |
| (57) | 200 | 5 |
| (58) | 200 | 5 |
| (59) | 200 | 5 |
| (60) | 200 | 5 |
| (61) | 200 | 5 |
| (62) | 200 | 5 |
| (63) | 200 | 5 |
| (64) | 200 | 5 |
| (65) | 200 | 5 |
| (66) | 200 | 5 |
| (67) | 200 | 5 |
| (68) | 200 | 5 |
| (69) | 200 | 5 |
| (70) | 200 | 5 |
| (71) | 200 | 5 |
| (72) | 200 | 5 |
| (73) | 200 | 5 |
| (74) | 200 | 5 |
| (75) | 200 | 5 |
| (76) | 200 | 5 |
| Reference compound A | 200 | 4 |

TEST EXAMPLE 3

Test for preventive controlling effect on sheath blight (*Rhizoctonia solani*) of rice Rice seeds (var.: Kinki No. 33) were sown in the sandy loam filled in a plastic pot. After raising for 28 days in a greenhouse, the seedlings were subjected to foliage application with a spray liquid of the suspension prepared according to Formulation Example 2 which was diluted with water to the given concentrations. After application, the seedlings were air-dried and then inoculated with mycelia of *Rhizoctonia solani* by spraying an agar suspension containing the fungi. The inoculated seedlings were grown in a dark damp place at 28° C. for 4 days, and the controlling effect was examined. The results are shown in Table 8.

TABLE 8

| Compound No. | Concentration of active ingredient (ppm) | Control effect |
|---|---|---|
| Present compound | | |
| (2) | 200 | 5 |
| (4) | 200 | 5 |

TABLE 8-continued

| Compound No. | Concentration of active ingredient (ppm) | Control effect |
| --- | --- | --- |
| (5) | 200 | 5 |
| (6) | 200 | 5 |
| (8) | 200 | 5 |
| (14) | 200 | 5 |
| (16) | 200 | 5 |
| (17) | 200 | 5 |
| (18) | 200 | 5 |
| (20) | 200 | 5 |
| (21) | 200 | 5 |
| (22) | 200 | 5 |
| (23) | 200 | 5 |
| (24) | 200 | 5 |
| (26) | 200 | 5 |
| (28) | 200 | 5 |
| (30) | 200 | 5 |
| (31) | 200 | 5 |
| (33) | 200 | 5 |
| (34) | 200 | 5 |
| (35) | 200 | 5 |
| (37) | 200 | 5 |
| (38) | 200 | 5 |
| (40) | 200 | 5 |
| (42) | 200 | 5 |
| (44) | 200 | 5 |
| (47) | 200 | 5 |
| (50) | 200 | 5 |
| (51) | 200 | 5 |
| (52) | 200 | 5 |
| (53) | 200 | 5 |
| (54) | 200 | 5 |
| (59) | 200 | 5 |
| (60) | 200 | 5 |
| (62) | 200 | 5 |
| (63) | 200 | 5 |
| (64) | 200 | 5 |
| (65) | 200 | 5 |
| (75) | 200 | 5 |
| Reference compound B | 60 | 4 |

TEST EXAMPLE 4

Test for preventive controlling effect on eyespot (*Pseudocercosporella herpotrichoides*) of wheat Wheat seeds (var.: Norin No. 73) were sown in the sandy loam filled in a plastic pot. After raising for 10 days in a greenhouse, the seedlings were subjected to foliage application with a spray liquid of the emulsion prepared according to Formulation Example 4 which was diluted with water to the given concentrations. After application, the seedlings were air-dried and then inoculated with MBC-resistant spores of *Pseudocercosporella herpotrichoides* by spraying a suspension containing the spore. The inoculated seedlings were grown in a dark damp place at 15° C. for 4 days, further incubated for 4 days under illumination, and the controlling effect was examined. The results are shown in Table 9.

TABLE 9

| Compound No. | Concentration of active ingredient (ppm) | Control effect |
| --- | --- | --- |
| Present compound | | |
| (1) | 500 | 5 |
| (2) | 500 | 5 |
| (3) | 500 | 5 |
| (4) | 500 | 5 |
| (5) | 500 | 5 |
| (6) | 500 | 5 |
| (7) | 500 | 5 |
| (8) | 500 | 5 |
| (9) | 500 | 5 |
| (10) | 500 | 5 |
| (11) | 500 | 5 |
| (12) | 500 | 5 |
| (13) | 500 | 5 |
| (14) | 500 | 5 |
| (15) | 500 | 5 |
| (16) | 500 | 5 |
| (17) | 500 | 5 |
| (18) | 500 | 5 |
| (19) | 500 | 5 |
| (20) | 500 | 5 |
| (21) | 500 | 5 |
| (22) | 500 | 5 |
| (23) | 500 | 5 |
| (24) | 500 | 5 |
| (25) | 500 | 5 |
| (26) | 500 | 5 |
| (27) | 500 | 5 |
| (28) | 500 | 5 |
| (29) | 500 | 5 |
| (30) | 500 | 5 |
| (31) | 500 | 5 |
| (32) | 500 | 5 |
| (33) | 500 | 5 |
| (34) | 500 | 5 |
| (35) | 500 | 5 |
| (36) | 500 | 5 |
| (37) | 500 | 5 |
| (38) | 500 | 5 |
| (39) | 500 | 5 |
| (40) | 500 | 5 |
| (41) | 500 | 5 |
| (43) | 500 | 5 |
| (44) | 500 | 5 |
| (46) | 500 | 5 |
| (47) | 500 | 5 |
| (48) | 500 | 5 |
| (49) | 500 | 5 |
| (50) | 500 | 5 |
| (51) | 500 | 5 |
| (52) | 500 | 5 |
| (53) | 500 | 5 |
| (54) | 500 | 5 |
| (55) | 500 | 5 |
| (56) | 500 | 5 |
| (57) | 500 | 5 |
| (58) | 500 | 5 |
| (59) | 500 | 5 |
| (60) | 500 | 5 |
| (61) | 500 | 5 |
| (62) | 500 | 5 |
| (63) | 500 | 5 |
| (64) | 500 | 5 |
| (65) | 500 | 5 |
| (66) | 500 | 5 |
| (67) | 500 | 5 |
| (68) | 500 | 5 |
| (70) | 500 | 5 |
| (71) | 500 | 5 |
| (72) | 500 | 5 |
| (73) | 500 | 5 |
| (74) | 500 | 5 |
| (75) | 500 | 5 |
| (76) | 500 | 5 |
| Reference compound C | 500 | 0 |

TEST EXAMPLE 5

Test for curative controlling effect on speckled leaf blotch (*Septoria tritici*) of wheat Wheat seeds (var.: Norin No. 73) were sown in the sandy loam filled in a plastic pot. After raising for 8 days in a greenhouse, the seedlings were inoculated with spores of *Septoria tritici* by spraying a suspension of spores. The inoculated seedlings were grown in a dark damp place at 15° C. for 3 days, and then grown for 4 days under lightening. The seedlings were subjected to foliage application with a spray liquid of the wettable powder prepared according to Formulation Example 1 which was diluted with water to the given concentration. After application, the seedlings were grown at 15° C. for 11 days under illumination, and the controlling effect was examined. The results are shown in Table 10.

TABLE 10

| Compound No. | Concentration of active ingredient (ppm) | Control effect |
| --- | --- | --- |
| Present compound | | |
| (1) | 200 | 5 |
| (2) | 200 | 5 |
| (3) | 200 | 5 |
| (4) | 200 | 5 |
| (5) | 200 | 5 |
| (6) | 200 | 5 |
| (7) | 200 | 5 |
| (8) | 200 | 5 |
| (9) | 200 | 5 |
| (10) | 200 | 5 |
| (11) | 200 | 5 |
| (13) | 200 | 5 |
| (14) | 200 | 5 |
| (15) | 200 | 5 |
| (16) | 200 | 5 |
| (17) | 200 | 5 |
| (18) | 200 | 5 |
| (19) | 200 | 5 |
| (20) | 200 | 5 |
| (21) | 200 | 5 |
| (22) | 200 | 5 |
| (23) | 200 | 5 |
| (24) | 200 | 5 |
| (25) | 200 | 5 |
| (26) | 200 | 5 |
| (27) | 200 | 5 |
| (28) | 200 | 5 |
| (29) | 200 | 5 |
| (30) | 200 | 5 |
| (31) | 200 | 5 |
| (32) | 200 | 5 |
| (33) | 200 | 5 |
| (34) | 200 | 5 |
| (35) | 200 | 5 |
| (36) | 200 | 5 |
| (37) | 200 | 5 |
| (38) | 200 | 5 |
| (39) | 200 | 5 |
| (40) | 200 | 5 |
| (41) | 200 | 5 |
| (42) | 200 | 5 |
| (43) | 200 | 5 |
| (44) | 200 | 5 |
| (45) | 200 | 5 |
| (46) | 200 | 5 |
| (47) | 200 | 5 |
| (48) | 200 | 5 |
| (49) | 200 | 5 |
| (50) | 200 | 5 |
| (51) | 200 | 5 |
| (52) | 200 | 5 |
| (54) | 200 | 5 |
| (55) | 200 | 5 |
| (56) | 200 | 5 |
| (57) | 200 | 5 |
| (58) | 200 | 5 |
| (59) | 200 | 5 |
| (60) | 200 | 5 |
| (61) | 200 | 5 |
| (62) | 200 | 5 |
| (63) | 200 | 5 |
| (64) | 200 | 5 |
| (65) | 200 | 5 |
| (66) | 200 | 5 |
| (67) | 200 | 5 |
| (68) | 200 | 5 |
| (69) | 200 | 5 |
| (70) | 200 | 5 |
| (71) | 200 | 5 |

TABLE 10-continued

| Compound No. | Concentration of active ingredient (ppm) | Control effect |
| --- | --- | --- |
| (72) | 200 | 5 |
| (73) | 200 | 5 |
| (74) | 200 | 5 |
| (75) | 200 | 5 |
| (76) | 200 | 5 |
| Reference compound E | 500 | 0 |

TEST EXAMPLE 6

Test for preventive controlling effect on scab (*Venturia inaequalis*) of apple

Apple seeds were sown in the sandy loam filled in a plastic pot. After raising for 20 days in a greenhouse, the seedlings, with the fourth to fifth foliage leaves open were subjected to foliage application with a spray liquid of the wettable powder prepared according to Formulation Example 1 which was diluted with water to the given concentrations. After application, the seedlings were air-dried and then inoculated with spores of *Venturia inaequalis* by spraying a suspension containing the spores. The inoculated seedlings were grown in a dark damp place at 15° C. for 4 days, and then grown under lightening for 15 days. The controlling effect was examined. The results are shown in Table 11.

TABLE 11

| Compound No. | Concentration of active ingredient (ppm) | Control effect |
| --- | --- | --- |
| Present compound | | |
| (2) | 500 | 5 |
| (4) | 500 | 5 |
| (5) | 500 | 5 |
| (6) | 500 | 5 |
| (7) | 500 | 5 |
| (11) | 500 | 5 |
| (15) | 500 | 5 |
| (17) | 500 | 5 |
| (20) | 500 | 5 |
| (21) | 500 | 5 |
| (22) | 500 | 5 |
| (24) | 500 | 5 |
| (27) | 500 | 5 |
| (28) | 500 | 5 |
| (29) | 500 | 5 |
| (30) | 500 | 5 |
| (32) | 500 | 5 |
| (33) | 500 | 5 |
| (35) | 500 | 5 |
| (39) | 500 | 5 |
| (40) | 500 | 5 |
| (42) | 500 | 5 |
| (43) | 500 | 5 |
| (44) | 500 | 5 |
| (49) | 500 | 5 |
| (52) | 500 | 5 |
| (57) | 500 | 5 |
| (61) | 500 | 5 |
| (63) | 500 | 5 |
| (68) | 500 | 5 |
| (74) | 500 | 5 |
| (75) | 500 | 5 |
| (76) | 500 | 5 |
| Reference compound D | 500 | 4 |

TEST EXAMPLE 7

Test for preventive controlling effect on anthracnose (*Colletotrichum lagenarium*) of cucumber Cucumber seeds (var.: *Sagami hanjiro*) were sown in the sandy loam filled in a plastic pot. After raising for 14 days in a greenhouse, the seedlings were subjected to foliage application with a spray liquid of the emulsion prepared according to Formulation Example 4 which was diluted with water to the given concentrations. After application, the seedlings were air-dried and then inoculated with spores of *Colletotrichum lagenarium* by spraying a suspension containing the spores. The inoculated seedlings were left to stand in a dark damp place at 23° C. for one day and then were grown under lightening for 4 days. The controlling effect was examined. The results are shown in Table 12.

TABLE 12

| Compound No. | Concentration of active ingredient (ppm) | Control effect |
|---|---|---|
| Present compound | | |
| (2) | 500 | 5 |
| (3) | 500 | 5 |
| (4) | 500 | 5 |
| (5) | 500 | 5 |
| (7) | 500 | 5 |
| (8) | 500 | 5 |
| (10) | 500 | 5 |
| (11) | 500 | 5 |
| (12) | 500 | 5 |
| (13) | 500 | 5 |
| (15) | 500 | 5 |
| (16) | 500 | 5 |
| (17) | 500 | 5 |
| (18) | 500 | 5 |
| (20) | 500 | 5 |
| (21) | 500 | 5 |
| (22) | 500 | 5 |
| (23) | 500 | 5 |
| (24) | 500 | 5 |
| (25) | 500 | 5 |
| (27) | 500 | 5 |
| (28) | 500 | 5 |
| (29) | 500 | 5 |
| (30) | 500 | 5 |
| (31) | 500 | 5 |
| (32) | 500 | 5 |
| (33) | 500 | 5 |
| (34) | 500 | 5 |
| (35) | 500 | 5 |
| (36) | 500 | 5 |
| (37) | 500 | 5 |
| (39) | 500 | 5 |
| (40) | 500 | 5 |
| (41) | 500 | 5 |
| (43) | 500 | 5 |
| (44) | 500 | 5 |
| (45) | 500 | 5 |
| (46) | 500 | 5 |
| (47) | 500 | 5 |
| (49) | 500 | 5 |
| (50) | 500 | 5 |
| (53) | 500 | 5 |
| (54) | 500 | 5 |
| (55) | 500 | 5 |
| (56) | 500 | 5 |
| (57) | 500 | 5 |
| (59) | 500 | 5 |
| (60) | 500 | 5 |
| (63) | 500 | 5 |
| (64) | 500 | 5 |
| (65) | 500 | 5 |
| (66) | 500 | 5 |
| (68) | 500 | 5 |
| (69) | 500 | 5 |
| (70) | 500 | 5 |
| (71) | 500 | 5 |
| (72) | 500 | 5 |
| (73) | 500 | 5 |
| (74) | 500 | 5 |
| (75) | 500 | 5 |
| (76) | 500 | 5 |

TABLE 12-continued

| Compound No. | Concentration of active ingredient (ppm) | Control effect |
|---|---|---|
| Reference compound D | 500 | 4 |

TEST EXAMPLE 8

Test for curative controlling effect on powdery mildew (*Erysiphe graminis* f. sp. *tritici*) of wheat Wheat seeds (var.: Norin No. 78) were sown in the sandy loam filled in a plastic pot. After raising for 10 days in a greenhouse, the seedlings were inoculated with spores of *Erysiphe graminis* f. sp. *tritici*. The inoculated seedlings were grown at 23° C. for 3 days. The seedlings were subjected to foliage application with a spray liquid of the suspension prepared according to Formulation Example 2 which was diluted with water to the given concentrations. After application, the seedlings were grown in a greenhouse at 23° C. for 7 days, and the controlling effect was examined. The results are shown in Table 13.

TABLE 13

| Compound No. | Concentration of active ingredient (ppm) | Control effect |
|---|---|---|
| Present compound | | |
| (3) | 500 | 5 |
| (4) | 500 | 5 |
| (5) | 500 | 5 |
| (6) | 500 | 5 |
| (14) | 500 | 5 |
| (15) | 500 | 5 |
| (16) | 500 | 5 |
| (17) | 500 | 5 |
| (18) | 500 | 5 |
| (19) | 500 | 5 |
| (20) | 500 | 5 |
| (21) | 500 | 5 |
| (22) | 500 | 5 |
| (23) | 500 | 5 |
| (24) | 500 | 5 |
| (25) | 500 | 5 |
| (27) | 500 | 5 |
| (28) | 500 | 5 |
| (29) | 500 | 5 |
| (31) | 500 | 5 |
| (35) | 500 | 5 |
| (36) | 500 | 5 |
| (37) | 500 | 5 |
| (39) | 500 | 5 |
| (42) | 500 | 5 |
| (44) | 500 | 5 |
| (47) | 500 | 5 |
| (49) | 500 | 5 |
| (51) | 500 | 5 |
| (52) | 500 | 5 |
| (59) | 500 | 5 |
| (60) | 500 | 5 |
| (62) | 500 | 5 |
| (63) | 500 | 5 |
| (64) | 500 | 5 |
| (65) | 500 | 5 |
| (68) | 500 | 5 |
| (70) | 500 | 5 |
| (71) | 500 | 5 |

TEST EXAMPLE 9

Test for preventive controlling effect on gray mold (*Botrytis cinerea*) of cucumber Cucumber seeds (var.: *Sagami hanjiro*) were sown in the sandy loam filled in a plastic pot. After raising for 14 days in a greenhouse, the seedlings were subjected to foliage application with a spray liquid of the emulsion prepared according to Formulation Example 4 which was diluted with water to the given concentrations. After application, the seedlings were air-dried and then inoculated with mycelia of *Botrytis cinerea* which is resistant to benzimidazole.thiophanate fungicide. The inoculated seedlings were grown in a dark damp place at 15° C. for 3 days, and the controlling effect was examined. The results are shown in Table 14.

TABLE 14

| Compound No. | Concentration of active ingredient (ppm) | Control effect |
|---|---|---|
| Present compound | | |
| (1) | 500 | 5 |
| (2) | 500 | 5 |
| (5) | 500 | 5 |
| (13) | 500 | 5 |
| (15) | 500 | 5 |
| (18) | 500 | 5 |
| (23) | 500 | 5 |
| (24) | 500 | 5 |
| (30) | 500 | 5 |
| (31) | 500 | 5 |
| (33) | 500 | 5 |
| (34) | 500 | 5 |
| (35) | 500 | 5 |
| (37) | 500 | 5 |
| (39) | 500 | 5 |
| (40) | 500 | 5 |
| (44) | 500 | 5 |
| (49) | 500 | 5 |
| (50) | 500 | 5 |
| (51) | 500 | 5 |
| (52) | 500 | 5 |
| (54) | 500 | 5 |
| (56) | 500 | 5 |
| (65) | 500 | 5 |
| (71) | 500 | 5 |
| Reference compound C | 500 | 0 |

TEST EXAMPLE 10

Test for curative controlling effect on leaf rust (*Puccinia recondita*) of wheat Wheat seeds (var.: Norin No. 73) were sown in the sandy loam filled in a plastic pot. After raising for 10 days in a greenhouse, the seedlings were inoculated with spores of *Puccinia recondita*. The inoculated seedlings were left to stand in a dark damp place for one day, and then subjecteed to foliage application with a spray liquid of the emulsion prepared according to Formulation Example 4 which was diluted with water to the given concentrations. After application, the seedlings were grown under lightening at 23° C. for 7 days. The controlling effect was examined. The test resuts are shown in Table 15.

TABLE 15

| Compound No. | Concentration of active ingredient (ppm) | Control effect |
|---|---|---|
| Present compound | | |
| (15) | 500 | 5 |
| (17) | 500 | 5 |
| (18) | 500 | 5 |
| (21) | 500 | 5 |
| (23) | 500 | 5 |
| (27) | 500 | 5 |
| (28) | 500 | 5 |
| (31) | 500 | 5 |
| (39) | 500 | 5 |
| (47) | 500 | 5 |

TABLE 15-continued

| Compound No. | Concentration of active ingredient (ppm) | Control effect |
|---|---|---|
| (60) | 500 | 5 |
| (71) | 500 | 5 |

TEST EXAMPLE 11

Test for preventive controlling effect on late blight (*Phytophthora infestans*) of tomato Tomato seeds (var.: Ponterosa) were sown in the sandy loam filled in a plastic pot. After raising for 20 days in a greenhouse, the seedlings, with the second to third foliage leaves open, were subjected to foliage application with a spray liquid of the wettable powder prepared according to Formulation Example 1 which was diluted with water to the given concentrations. After application, the seedlings were air-dried and then inoculated with *Phytophthora infestans* by spraying a suspension containing the spores. The inoculated seedlings were grown in a damp place at 20° C. for one day, and then grown in a greenhouse for 5 days, and the controlling effect was examined. The results are shown in Table 16.

TABLE 16

| Compound No. | Concentration of active ingredient (ppm) | Control effect |
|---|---|---|
| Present compound | | |
| (6) | 500 | 5 |
| (11) | 500 | 5 |
| (15) | 500 | 5 |
| (18) | 500 | 5 |
| (23) | 500 | 5 |
| (27) | 500 | 5 |
| (34) | 500 | 5 |
| (35) | 500 | 5 |
| (43) | 500 | 5 |
| (71) | 500 | 5 |
| (74) | 500 | 5 |
| (75) | 500 | 5 |
| (76) | 500 | 5 |

We claim:

1. A pyridinylpyrimidine derivative of the formula:

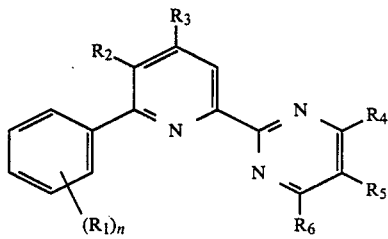

or a salt thereof,
wherein $R_1$ may be the same or different and is lower alkyl, lower alkoxy, lower haloalkyl or halogen; n is 0, 1, 2, 3, 4 or 5; $R_2$ and $R_3$, which may be the same or different, each represent hydrogen or lower alkyl; $R_4$ is hydrogen or lower alkyl; $R_5$ is hydrogen, lower alkyl or halogen, or $R_4$ and $R_5$ together represent a polymethylene group of the formula: $-(CH_2)_m-$ in which m is 3 or 4; and $R_6$ is hydrogen, lower alkyl, lower alkoxy or lower-alkylthio.

2. A pyridinylpyrimidine derivative according to claim 1, wherein $R_1$ may be the same or different and is $C_1$-$C_3$ alkyl, $C_1$-$C_3$ alkoxy, $C_1$-$C_3$ haloalkyl or halogen; n is 0, 1 or 3; $R_2$ is hydrogen or methyl; $R_3$ is hydrogen or $C_1$-$C_4$ alkyl; $R_4$ is hydrogen, methyl or ethyl; $R_5$ is hydrogen, methyl, ethyl or halogen and $R_6$ is hydrogen, methyl, ethyl, methoxy, ethoxy or methylthio.

3. A pyridinylpyrimidine derivative according to claim 1, wherein $R_1$ may be the same or different and is methyl, ethyl, methoxy, $C_1$ or $C_2$ haloalkyl or halogen, n is 0, 1, 2 or 3, $R_2$ and $R_3$, which may be the same or different, each represent hydrogen or methyl, $R_4$ is methyl, $R_5$ is hydrogen or methyl, and $R_6$ is hydrogen, methyl or methoxy.

4. A pyridinylpyrimidine derivative according to claim 1, wherein $R_1$ may be the same or different and is methyl, trifluoromethyl, fluorine or chlorine, n is 0, 1 or 2, $R_2$ is hydrogen or methyl, $R_3$ is hydrogen, $R_4$ is methyl, $R_5$ is hydrogen or methyl and $R_6$ is hydrogen or methyl.

5. 4-Methyl-2-(6-phenyl-2-pyridinyl)pyrimidine or a salt thereof.

6. 4-Methyl-2-(5-methyl-6-phenyl-2-pyridinyl)-pyrimidine or a salt thereof.

7. 4,5-Dimethyl-2-(5-methyl-6-phenyl-2-pyridinyl)-pyrimidine or a salt thereof.

8. 4-Methyl-2-(5-methyl-6-p-tolyl-2-pyridinyl)pyrimidine or a salt thereof.

9. 2-(6-o-Chlorophenyl-2-pyridinyl)-4-methylpyrimidine or a salt thereof.

10. 2-(6-o-Chlorophenyl-5-methyl-2-pyridinyl)-4-methylpyrimidine or a salt thereof.

11. 4-Methyl-2-(6-α,α,α-trifluoro-o-tolyl-2-pyridinyl)pyrimidine or a salt thereof.

12. 4,6-Dimethyl-2-(6-phenyl-2-pyridinyl)pyrimidine or a salt thereof.

13. 4-Methoxy-6-methyl-2-(6-phenyl-2-pyridinyl)-pyrimidine or a salt thereof.

14. 2-(6-m-Chlorophenyl-2-pyridinyl)-4-methoxy-6-methylpyrimidine or a salt thereof.

15. A plant disease protectant which comprises as an active ingredient an effective amount of a pyridinylpyrimidine derivative of the formula:

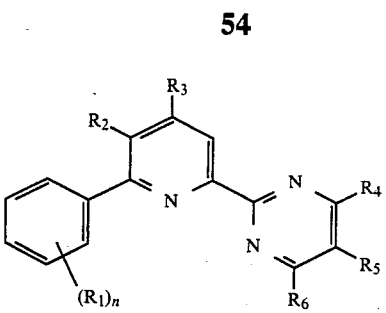

or a salt thereof, wherein $R_1$ may be the same or different and is lower alkyl, lower alkoxy, lower haloalkyl or halogen; n is 0, 1, 2, 3, 4 or 5; $R_2$ and $R_3$, which may be the same or different, each represent hydrogen or lower alkyl; $R_4$ is hydrogen or lower alkyl; $R_5$ is hydrogen, lower alkyl or halogen, or $R_4$ and $R_5$ together represent a polymethylene group of the formula: $-(CH_2)_m-$ in which m is 3 or 4; and $R_6$ is hydrogen, lower alkyl, lower alkoxy or lower alkylthio, and an inert carrier.

16. A plant disease protectant which comprises as an active ingredient an effective amount of the pyridinylpyrimidine derivative or a salt thereof as claimed in any one of claims 2 to 14 and an inert carrier.

17. A method for controlling plant pathogenic fungi which comprises applying to plant pathogenic fungi an effective amount of the pyridinylpyrimidine derivative of the formula:

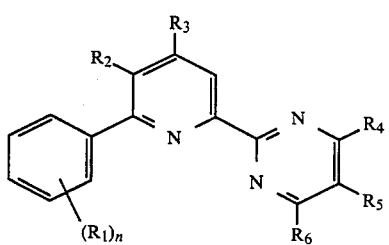

or a salt thereof, wherein $R_1$ may be the same or different and is lower alkyl, lower alkoxy, lower haloalkyl or halogen; n is 0, 1, 2, 3, 4 or 5; $R_2$ and $R_3$, which may be the same or different, each represent hydrogen or lower alkyl; $R_4$ is hydrogen or lower alkyl; $R_5$ is hydrogen, lower alkyl or halogen, or $R_4$ and $R_5$ together represent a polymethylene group of the formula: $-(CH_2)_m-$ in which m is 3 or 4; and $R_6$ is hydrogen, lower alkyl, lower alkoxy or lower alkylthio.

* * * * *